US011011276B2

(12) United States Patent
Chen et al.

(10) Patent No.: US 11,011,276 B2
(45) Date of Patent: May 18, 2021

(54) METHOD FOR ESTABLISHING COMPUTER-AIDED DATA INTERPRETATION MODEL FOR IMMUNE DISEASES BY IMMUNOMARKERS AND VISUALIZATION

(71) Applicants: Chun-Hsien Chen, Taoyuan (TW); Yi-Ju Tseng, Taoyuan (TW); Hsin-Yao Wang, Chiayi (TW); Wan-Ying Lin, Taipei (TW); Chih-Kuang Chen, Taipei (TW)

(72) Inventors: Chun-Hsien Chen, Taoyuan (TW); Yi-Ju Tseng, Taoyuan (TW); Hsin-Yao Wang, Chiayi (TW); Wan-Ying Lin, Taipei (TW); Chih-Kuang Chen, Taipei (TW)

(73) Assignees: CHANG GUNG MEMORIAL HOSPITAL, LINKOU, Taoyuan (TW); CHANG GUNG UNIVERSITY, Taoyuan (TW)

( * ) Notice: Subject to any disclaimer, the term of this patent is extended or adjusted under 35 U.S.C. 154(b) by 431 days.

(21) Appl. No.: 16/029,726

(22) Filed: Jul. 9, 2018

(65) Prior Publication Data

US 2020/0013513 A1 Jan. 9, 2020

(51) Int. Cl.
*G06F 3/048* (2013.01)
*G16H 50/50* (2018.01)
*G06N 20/00* (2019.01)

(52) U.S. Cl.
CPC ............. *G16H 50/50* (2018.01); *G06N 20/00* (2019.01)

(58) Field of Classification Search
None
See application file for complete search history.

(56) References Cited

U.S. PATENT DOCUMENTS

| | | | |
|---|---|---|---|
| 2008/0133141 A1* | 6/2008 | Frost | G01N 33/6848 702/19 |
| 2016/0299144 A1* | 10/2016 | Blume | G01N 33/57419 |

OTHER PUBLICATIONS

Tommaso et al., Diagnostic Accuracy of Clathrin Heavy Chain Stainingin a Marker Panel for the Diagnosis of Small Hepatocellular Carcinoma, HEPATOLOGY, vol. 53, No. 5, 2011, 1549-1557 (Year: 2011).*

* cited by examiner

*Primary Examiner* — William C Trapanese

(57) ABSTRACT

A method for establishing a computer-aided data interpretation model for immune diseases by immunomarkers and visualization is revealed. First combine a plurality of immunomarkers into an immunomarker panel. Then collect test data of a plurality of subjects measured by the immunomarker panel, and disease diagnosis information of the subjects for establishment of an immunomarker-panel testing database. Next new subjects are tested by the immunomarker panel. The data obtained and the corresponding information in the immunomarker-panel testing database are processed by unsupervised machine learning algorithm to get a computer-aided data interpretation model showing comparison of case distribution patterns. The method provides real-time analysis of multiple data to medical professionals for their reference. Thereby the correctness, the timeliness and the reproducibility of the interpretation result for the diagnosis and treatment of immune diseases are all improved.

7 Claims, 3 Drawing Sheets

METHOD FOR ESTABLISHING COMPUTER-AIDED DATA INTERPRETATION MODEL FOR IMMUNE DISEASES BY IMMUNOMARKERS AND VISUALIZATION

BACKGROUND OF THE INVENTION

Field of the Invention

The present invention relates to a method for establishing a computer-aided data interpretation model, especially to a method for establishing a computer-aided data interpretation model for immune diseases by immunomarkers and visualization that provides real-time analysis by using immunomarker panels in combination with machine learning mechanism. Comparison results are shown in diagrams and users can determine possible immune diseases of new target cases according to the overall data distribution.

Description of Related Art

Immune diseases are major diseases in many developing countries and developed countries. There are various types of immune diseases and several criteria are required for diagnosis confirmation. According to literatures various literature, a diagnosis could not be confirmed among approximately 20%-52% patients with immune diseases. Moreover, certain immune diseases have slow disease progression and their clinical manifestation at early stage is not typical, and therefore patients are unable to get confirmed diagnosis and proper treatment during long follow-up. Thus, the diagnosis, treatment and follow-up for patients with immune diseases are incorrect, uneconomic and inconvenient. This causes a huge waste of medical resources.

Most immune diseases are detected by testing of immunomarker panels. The test values (test results) measured by the immunomarker panel, including a plurality of immunomarkers, are frequently interpreted by medical staff. Therefore, the interpretation lacks timeliness and accuracy. The interpretation is based on the reference values/thresholds of those immunomarkers. Once the test value of any single immunomarker exceeds its reference value, it is predicted that the subject has the potential to develop the immune diseases. However, a comprehensive distribution pattern of the overall massive data cannot be provided by the traditional method in routine clinical practice.

Moreover, in management of immune diseases, there is no feasible technique currently available for diagnosis and follow-up of Undifferentiated Connective Tissue Disease (UCTD) in order to give patients proper treatment for UCTD. Clinical diagnosis and treatment of UCTD largely depends on individual medical professionals' experience. Furthermore, the test methods currently available have certain shortcomings including lack of objectivity, high cost, and patients may be exposed to potential iatrogenic effects.

Thus there is room for improvement and there is a need to provide a novel method that helps medical staff to understand, diagnose and track the progression of UCTD conveniently and objectively.

SUMMARY OF THE INVENTION

Therefore a primary objective of the present invention is to provide a method for establishing a computer-aided data interpretation model for immune diseases by immunomarkers and visualization by which doctors can refer to case distribution patterns in the computer-aided data interpretation model for marking characteristics of the immune diseases of new subjects, tracking the progression changes of new subjects over time, and diagnosing immune diseases. Accordingly, the correctness, the timeliness and the reproducibility of the interpretation for disease testing result are all improved.

Another objective of the present invention is to provide a method for establishing a computer-aided data interpretation model for tracking the temporal progression of immune diseases. New subjects can be tested at different times and a plurality of test results are displayed in the computer-aided data interpretation model. Thus clinical staff can observe the multiple test results of the patients at different time and observe how the disease progresses over time. Or the test data of the new subjects is tested at single time point and displayed on the computer-aided data interpretation model to show the distributive comparison of the new subjects over the cases in the database. A correlation between a new patient and the cases in database can also be provided. Moreover, the relative relationship between the new patient's disease and the given diseases can be objectively learned by comparing the temporal track of new patient's data pattern with those of the given diseases. Therefore, the diagnosis or tracking of known immune diseases or undefined immune diseases can be improved by the data visualization tool of our invention.

In order to achieve the above objectives, a method for establishing a computer-aided data interpretation model for immune diseases by immunomarkers and visualization methods according to the present invention includes the following steps. (1) First combine a plurality of immunomarkers into an immunomarker panel. (2) Then collect both test data of a plurality of subjects by testing of the immunomarker panel, and disease diagnosis information of the subjects to establish an immunomarker-panel testing database. (3) Compare new subjects' test data with information in the computer-aided data interpretation model. The test data of the new subjects is obtained by the following way. Select at least two immunomarkers in the immunomarker panel and then retrieve information corresponding to the immunomarkers tested in the immunomarker-panel testing database to be compared and analyzed by unsupervised machine learning algorithms. The results are displayed in diagrams on the computer-aided data interpretation model for the comparison of case distribution patterns.

As to the immunomarker panel, it's used to get a plurality of test values (test parameters) for description of the diseases. The subject/individual can get a plurality of test results in a single test for diagnosis of possible immune diseases.

The subject only needs to take the test once and spends minimal time for the test so that both convenience and timeliness are improved. The immunomarker-panel testing database established by a plurality of immunomarker panels and the corresponding disease diagnosis information contains lots of test data therein so that medical staff can learn more about characteristics of the immune disease. The unsupervised machine learning algorithm provides a real-time analysis of data/test results. Thus the data available now can be analyzed and classified into different diseases. The graphical representation of the analysis results can show the changes in distribution for clinicians' reference.

BRIEF DESCRIPTION OF THE DRAWINGS

The structure and the technical means adopted by the present invention to achieve the above and other objectives can be best understood by referring to the following detailed description of the preferred embodiments and the accompanying drawings, wherein.

DETAILED DESCRIPTION OF THE PREFERRED EMBODIMENT

Figure 1:
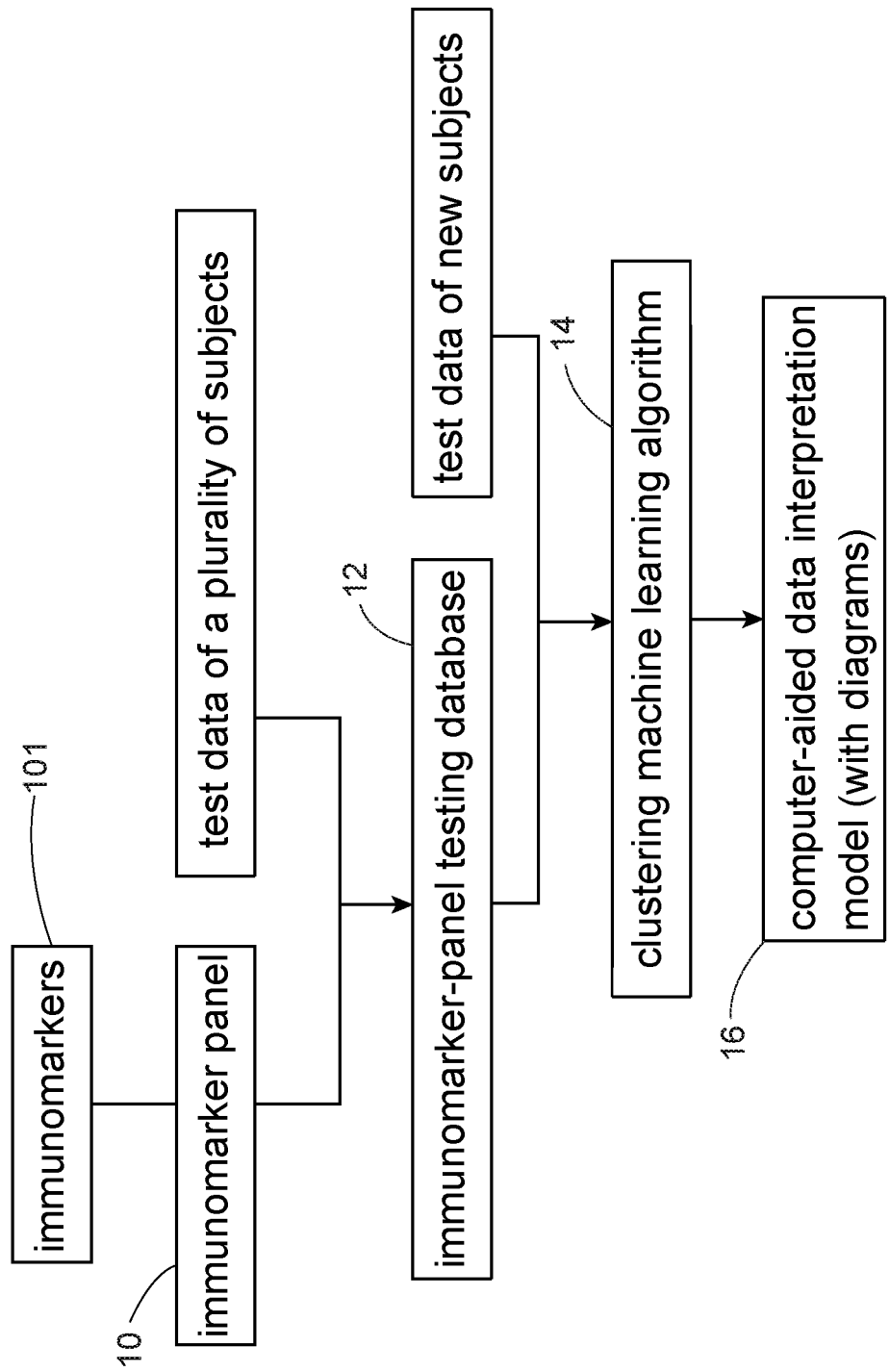
FIG. 1 is a flow chart showing steps of an embodiment according to the present invention.

Refer to FIG. 1, a method for establishing a computer-aided data interpretation model for immune diseases by immunomarkers and visualization according to the present invention includes the following steps. (1) first combining a plurality of immunomarkers 101 into an immunomarker panel 10; (2) collecting both test data of a plurality of subjects obtained by testing of the immunomarker panel 10, and disease diagnosis information corresponding to the subjects to establish an immunomarker-panel testing database 12; (3) Select at least two immunomarkers 101 in the immunomarker panel 10 to perform tests and get the test data of the new subjects. Then pick up corresponding data of the immunomarkers 101 tested in the immunomarker-panel testing database 12. Both the test data of the new subjects and the corresponding data in the immunomarker-panel testing database 12 are entered into a machine learning platform for making comparison and analysis by unsupervised machine learning algorithm 14 in the machine learning platform. Next the results are shown in diagrams on the computer-aided data interpretation model 16 for comparing case distribution patterns visually. With the assistance of the case distribution patterns in the visualized computer-aided data interpretation model 16, medical professionals can evaluate disease characteristics of the new subjects objectively.

The tests for obtaining the test data of the new subjects can be carried out at several different time points and then displayed on the computer-aided data interpretation model 16 simultaneously to show changes of the test data of the new subjects over time.

Figure 2:
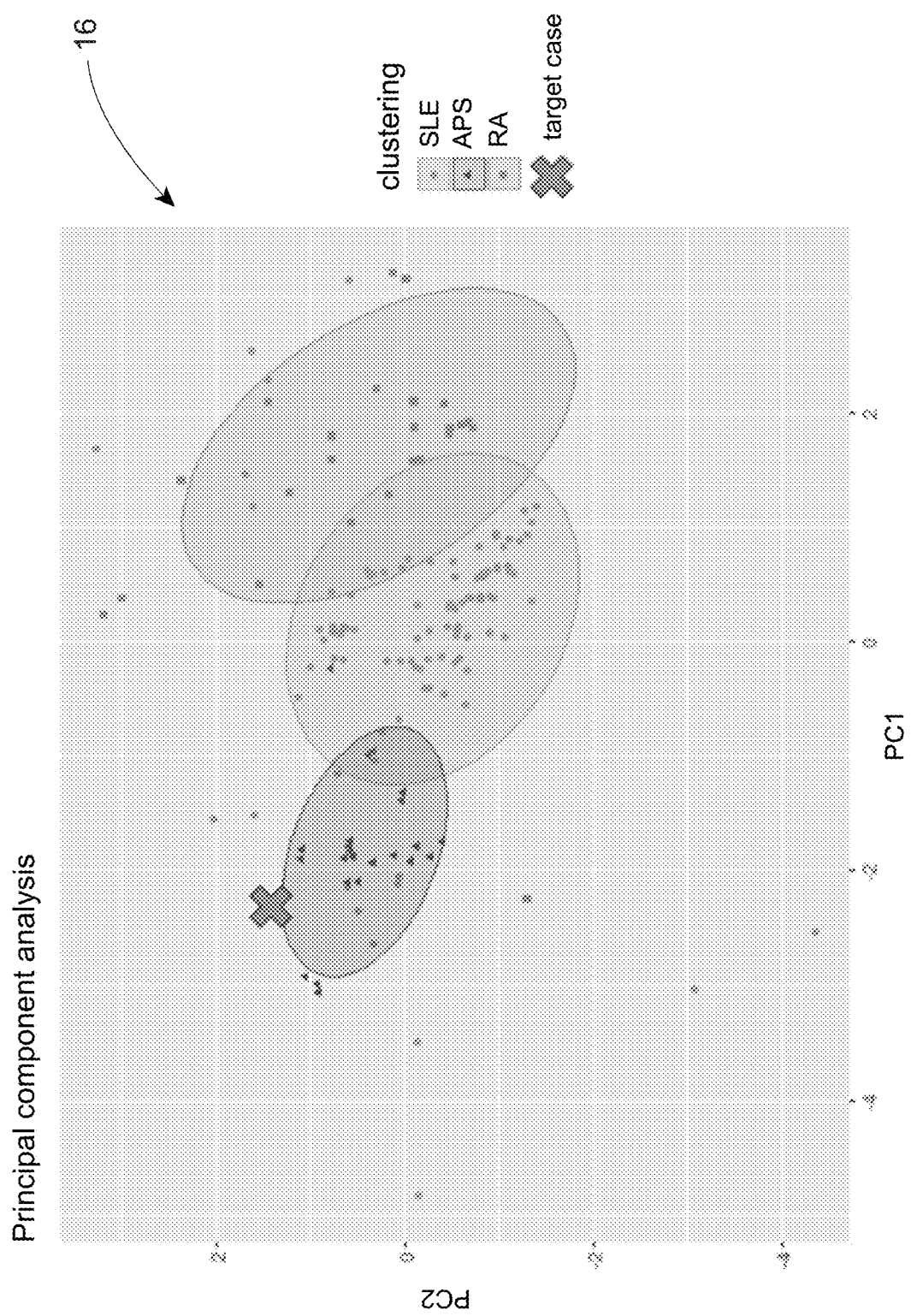
FIG. 2 is a principal component analysis (PCA) showing the clustering relationship between a target case and the cases in a database of the embodiment according to the present invention; PC1: first principal component; PC2: second principal component; SLE: Systemic Lupus Erythematosus; APS: Antiphospholipid syndrome; RA: Rheumatoid arthritis.
Figure 3:
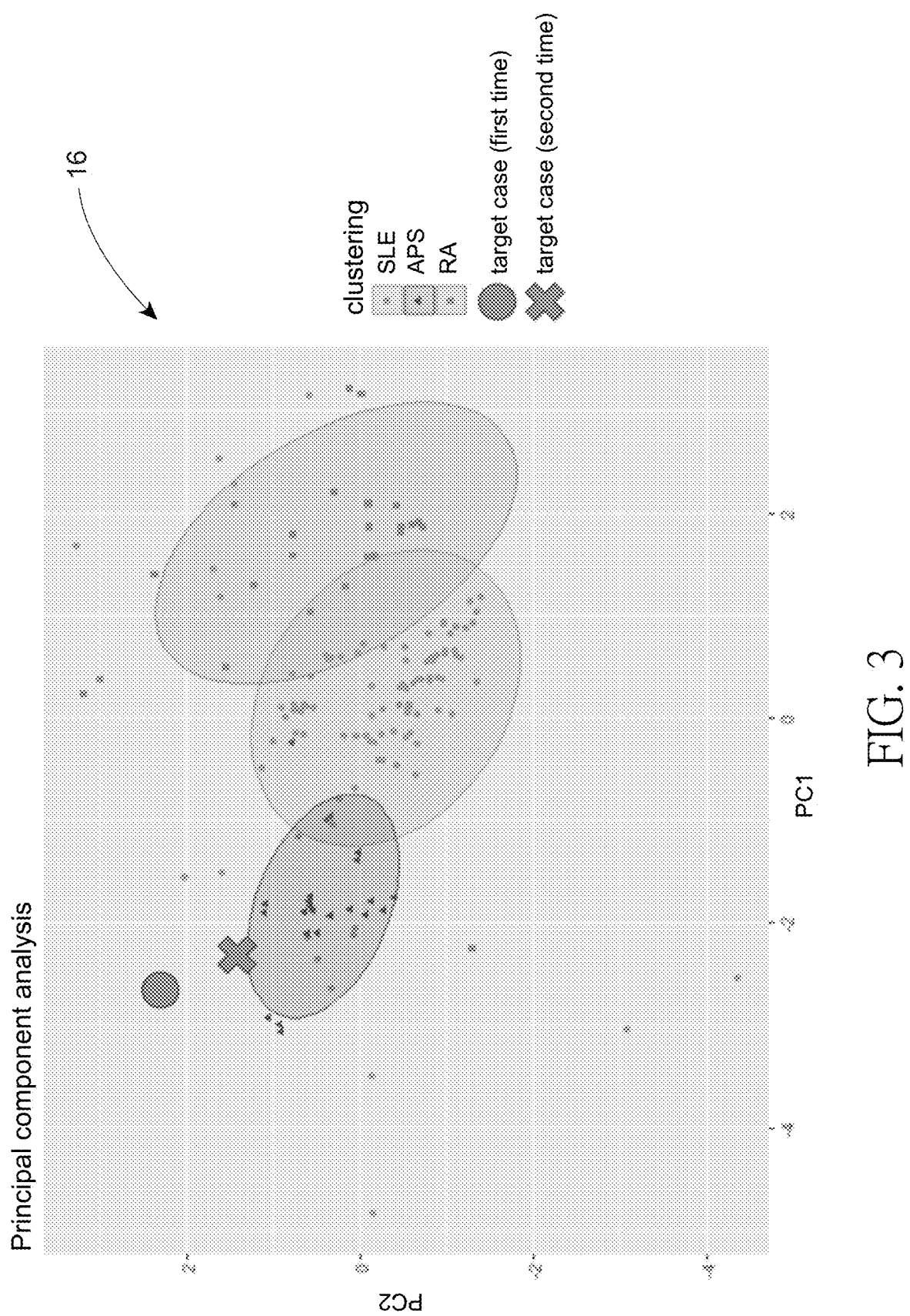
FIG. 3 is a principal component analysis (PCA) showing a change of the target case over time in the embodiment according to the present invention. PC1: first principal component; PC2: second principal component; SLE, APS, and RA.

Refer to FIG. 1, FIG. 2 and FIG. 3, a computer-aided data interpretation model 16 established by an embodiment of the present invention based on test results of patients with immune diseases at a medical center in Taiwan is revealed. The tests are carried out by using the immunomarker panel 10.

1. Conditions (including admission and exclusion) of individuals being screened and the number of samples: the subjects tested by the immunomarker panel 10 are adults older than 20 years. A retrospective chart review is used in this embodiment so that recruitment of the subjects is not required.

2. Retrospective period of the embodiment: from Jan. 1, 2013 to Dec. 31, 2015.

3. Design and method:

(1) First collect samples of 160 adults (called cases) and use the immunomarker panel 10 to test the samples. The samples obtained from the cases include blood, urine, saliva, sweat, feces, pleural fluid, ascites fluid or cerebrospinal fluid. In this embodiment, there are eight immunomarkers 101 contained in the immunomarker panel 10 and are used as test parameters, including anti-cardiolipin antibody IgG (ACAG), anti-cardiolipin antibody IgM (ACAM), β2-glycoprotein 1 IgG (B2GP1G), β2-glycoprotein 1 IgM (B2GP1M), anti-phospholipid IgG (APHLG), anti-phospholipid IgM (APHLM), anti-nucleus antibody (ANA) and lupus cell.

(2) Use the data of the 160 cases obtained by testing of the immunomarker panel 10 and the disease diagnosis information of the respective cases obtained by retrospective chart review to build up an immunomarker-panel testing database 12. In the FIG. 2 and FIG. 3, PC1 is the first principal component while PC2 is the second principal component. SLE means systemic lupus erythematosus. APS means antiphospholipid syndrome. RA means rheumatoid arthritis.

(3) The new subjects (called target cases) can select at least two immunomarkers 101 as test items of the immunomarker panel 10. The test results of the immunomarker panel 10 are entered into a machine learning platform while information corresponding to the immunomarkers 101 tested in the immunomarker-panel testing database 12 is also retrieved and entered into the machine learning platform. Then data of the test results and the corresponding information are processed by unsupervised machine learning algorithm 14 in the machine learning platform and a scatter plot is used to show the clustering relationship between cases in the immunomarker-panel testing database 12 and the target case.

(4) Once the analysis result of a single test of the new subject is not close to any cluster apparently in the scatter plot built by the computer-aided data interpretation model 16, the new subject is informed to be tested by the immunomarker panel 10 again at other later times. The medical staff can get information of the corresponding immunomarkers 101 in the immunomarker-panel testing database 12 according to the immunomarkers 101 in the immunomarker panel 10 tested for the new subject. By the principal component analysis (PCA), the information of the cases in the immunomarker-panel testing database 12 and changes in the test data of the target case over time are displayed (FIG. 3).

Effect:

After being analyzed by the principal component analysis (PCA), the multi-dimensional complicated data in the immunomarker-panel testing database 12 are converted and projected to diagrams for establishment of the computer-aided data interpretation model 16. Thereby medical staff can easily learn the degree of correlation between the target cases and the cases in the immunomarker-panel testing database 12 by a 2-dimensional graph of the computer-aided data interpretation model 16. Refer to FIG. 2, the clinical presentation of the target case seems consistent to UCTD. By the computer-aided data interpretation model 16, the target case and the cases in the immunomarker-panel testing database 12 can be displayed and compared visually. In this embodiment, the location of the target case is close to the case distribution of the APS group. The data represented by visualization of the computer-aided data interpretation model 16 reminds the clinical staff that the target case is possible to develop APS in the future. After getting such information, the medical staff and patients can perform further related medical tests and examinations for treatment and risk control. The present method can be applied to reduce diagnostic uncertainty at initial or early stage of immune diseases in clinical practice. Thus the cost of medical tests and examinations and medical expenses associated with patients with frequent visits are further reduced.

Refer to FIG. 3, the first test result and the second test result of the target case tested by the immunomarker panel 10 are displayed. The data of the above test results of the immunomarker panel 10 and information in the immunomarker-panel testing database 12 are processed by PCA projection on the first PC (PC1) and the second PC (PC2). The PCA projection of the first test result of the target case is not typical so that it's difficult to directly determine whether the target case is close enough a specific group of the immune disease. After the first test result in combination with the second test result of the target case are represented visually at the same time, it is found that the result test of the target case is gradually moved closely to the case distribution cluster of the APS group. According to such data visualization, the medical professionals have an objective criterion for predicting disease progression of the target case and arranging appropriate tests, examinations and treatment.

The above unsupervised machine learning algorithm is principal component analysis (PCA), self-organizing map (SOM), hierarchical clustering, k-means clustering, k-medoids clustering, expectation-maximization clustering, density-based clustering methods, grid-based clustering methods, model-based clustering methods, or a combination thereof.

The immunomarkers include anti-cardiolipin antibody IgG (ACAG), anti-cardiolipin antibody IgM (ACAM), β2-glycoprotein 1 IgG (B2GP1G), β2-glycoprotein 1 IgM (B2GP1M), anti-phospholipid IgG (APHLG), anti-phospholipid IgM (APHLM), anti-nucleus antibody (ANA), rheumatoid factor, lupus cell, hs-CRP, anti-ds DNA Ab, anti-ss DNA Ab, anti-Ribosomal-P antibody, anti-ENA Ab, anti-thyroglobulin antibody, anti-TPO Ab, ANCA, Anti-SSA antibody, Anti-SSB antibody, anti-Smith antibody, anti-RNP Ab, anti-Ku antibody, anti-Ro52 antibody, anti-hnRNP protein A1 antibody, anti-PCNA antibody, anti-Hsp90 antibody, anti-Golgi complex antibody, anti-HMG 17 antibody, anti-Scl 70 antibody, anti-centromere antibody, anti-RNA Polymerase I antibody, anti-RNA Polymerase II antibody, anti-RNA Polymerase III antibody, anti-fibrillarin antibody, anti-U1 RNP antibody, anti-PM Scl antibody, anti-Th antibody, anti-NOR 90 antibody, anti-muscarinic receptor antibody, anti-α fodrin antibody, anti-NA 14 antibody, anti-Jo 1 antibody, anti-PL 7 antibody, anti-PL 12 antibody, anti-Zo antibody, anti-YRS antibody, anti-KS antibody, anti-EJ antibody, anti-OJ antibody, anti-MDA 5 Ab, anti-Mi 2 antibody, anti-SRP Ab, anti-SAE Ab, anti-p155 antibody, anti-HMGCR antibody, anti-MJ antibody and a combination thereof

What is claimed is:

1. A method for establishing a computer-aided data interpretation model for immune diseases by immunomarkers and visualization comprising the steps of:
   (1) combining a plurality of immunomarkers into an immunomarker panel;
   (2) collecting test data of a plurality of subjects measured by the immunomarker panel, and disease diagnosis information corresponding to the plurality of subjects to build up an immunomarker-panel testing database;
   (3) obtaining test data of a new subject by testing of at least two of the plurality of immunomarkers;
   (4) entering the test data into a machine learning platform and retrieving information corresponding to the immunomarkers tested from the immunomarker-panel testing database to be compared and analyzed by an unsupervised machine learning algorithm in the machine learning platform; and
   (5) generating a computer-aided data interpretation model showing a comparison of visualized case distribution patterns,
      wherein a scatter plot is generated and illustrates a relationship between subjects in the immunomarker-panel testing database and the new subject, and
      wherein when a determination is made that a single test of the new subject is not close to any cluster in the scatter plot, the new subject is advised to be tested at a later time.

2. The method of claim 1, wherein the test data of the new subjects is tested at single time point and displayed on the computer-aided data interpretation model to show the distributive comparison of the new subjects over the cases in the database.

3. The method of claim 1, wherein the test data of the new subjects is tested at multiple different time points and displayed on the computer-aided data interpretation model at the same time to show changes in the test data of the new subjects over time.

4. The method of claim 1, wherein the unsupervised machine learning algorithm is selected from the group consisting of principal component analysis (PCA), self-organizing map (SOM), hierarchical clustering, k-means clustering, k-medoids clustering, expectation-maximization clustering, density-based clustering methods, grid-based clustering methods, model-based clustering methods, and a combination thereof.

5. The method of claim 1, wherein samples from the subjects and the new subjects include blood, urine, saliva, sweat, feces, pleural fluid, ascites fluid or cerebrospinal fluid.

6. The method of claim 1, wherein the immunomarkers include anti-cardiolipin antibody IgG (ACAG), anti-cardiolipin antibody IgM (ACAM), μ2-glycoprotein 1 IgG (B2GP1G), μ2-glycoprotein 1 IgM (B2GP1M), anti-phospholipid IgG (APHLG), anti-phospholipid IgM (APHLM), anti-nucleus antibody (ANA), rheumatoid factor, lupus cell, hs-CRP, anti-ds DNA Ab, anti-ss DNA Ab, anti-Ribosomal-P antibody, anti-ENA Ab, anti-thyroglobulin antibody, anti-TPO Ab, ANCA, Anti-SSA antibody, Anti-SSB antibody, anti-Smith antibody, anti-RNP Ab, anti-Ku antibody, anti-Ro52 antibody, anti-hnRNP protein A1 antibody, anti-PCNA antibody, anti-Hsp90 antibody, anti-Golgi complex antibody, anti-HMG 17 antibody, anti-Scl 70 antibody, anti-centromere antibody, anti-RNA Polymerase I antibody, anti-RNA Polymerase II antibody, anti-RNA Polymerase III antibody, anti-fibrillarin antibody, anti-U1 RNP antibody, anti-PM Scl antibody, anti-Th antibody, anti-NOR 90 antibody, anti-muscarinic receptor antibody, anti-a fodrin antibody, anti-NA 14 antibody, anti-Jo 1 antibody, anti-PL 7 antibody, anti-PL 12 antibody, anti-Zo antibody, anti-YRS antibody, anti-KS antibody, anti-EJ antibody, anti-OJ antibody, anti-MDA 5 Ab, anti-Mi 2 antibody, anti-SRP Ab, anti-SAE Ab, anti-p155 antibody, anti-HMGCR antibody, anti-MJ antibody and a combination thereof.

7. The method of claim 1, wherein the immunomarker panel is used to test immune diseases.

* * * * *